(12) United States Patent
Cheney et al.

(10) Patent No.: US 6,531,646 B1
(45) Date of Patent: Mar. 11, 2003

(54) STRAIN MANIPULATION AND IMPROVEMENT IN THE EDIBLE SEAWEED PORPHYRA

(75) Inventors: Donald P. Cheney, Ipswich, MA (US); Kathryn M. Roberts, Melrose, MA (US); Katherine L. Watson, Dover, NH (US)

(73) Assignee: Northeastern University, Boston, MA (US)

( * ) Notice: Subject to any disclaimer, the term of this patent is extended or adjusted under 35 U.S.C. 154(b) by 0 days.

(21) Appl. No.: 09/581,371

(22) PCT Filed: Dec. 11, 1998

(86) PCT No.: PCT/US98/26464
§ 371 (c)(1),
(2), (4) Date: Jun. 12, 2000

(87) PCT Pub. No.: WO99/29160
PCT Pub. Date: Jun. 17, 1999

Related U.S. Application Data

(60) Provisional application No. 60/069,563, filed on Dec. 12, 1997.

(51) Int. Cl.$^7$ .................. C12N 15/05; C12N 15/82; C12N 15/08; A01H 11/00; A01H 13/00
(52) U.S. Cl. .................. 800/277; 800/295; 800/296; 800/292; 435/421; 435/420; 435/419; 435/430; 435/410; 435/440; 435/449; 435/450; 435/453; 435/454
(58) Field of Search .................. 800/277, 292, 800/295, 296; 435/421, 420, 419, 430, 410, 440, 449, 450, 453, 454

(56) References Cited

PUBLICATIONS

Yamazaki et al., "Phylogenetic Position of *Porpyhra yezoensis* Based on the 18S rDNA Sequence", Journal of Marine Biotechnology, 4(4) 230–232 (1996).
Bird et al., "Towards an 18S Ribosomal RNA Gene Phylogeny of the Red Algae (Rhodophyta)", Int, Marine Biotechnology Conference (IMBC '91), Baltimore, MD, USA, p. 84, Oct. 13–16, 1994.
Kapraun et al., "Karyology and Cytophotometric Estimation of Inter– and Intraspecific Nuclear DNA Variation in Four Species of Porphyra (Rodophyta)", Phycologia, Sep. 1991, vol. 30, No. 5, pp. 458–477, (1991).
Waaland et al., Protoplast Isolation and Regeneration in the Marine Red Algae Porphyra nereocJystis, Planta, vol. 181, pp. 522–528, (1990).
Fujita et al., "Fusion of Protoplasts from Thalli of Two Different Color Types in *Porphyra yezoensis* UEDA and Development of Fusion Products", The Japanese Journal of Phycology, pp. 201–208, Sep. 20, 1997.
Coll et al., "The Nuclear State of Reproductive Cells of *Porphyra leucosticta* Thuret in Le Jolis" Phycologia, vol. 16, No. 3, pp. 227–229, Sep. 1997.
Evans D. A., "Agricultural Application of Plant Protoplast Fusion" Bio/Technology, pp. 253–261 May 1983.
Japanese Patent Abstracts, Week 198648, London: Derwent Publications Ltd., Class D13, AN 1986–314108, JP 61212281 A (Shiraha A) Sep. 20, 1986.
Japanese Patent Abstracts, Week 168542, London: Derwent Publications Ltd., Class D16, An 1985–261177, JP 60176582 A (Koasa Shoji) Sep. 10, 1985.
Waaland et al., "Conchospore production and seasonal occurrence of some Porphyra species (Bangiales, Rhodophyta) in Washington State", Hydrobiologia, 204/205: 453–459 (1990).
Mukai et al., "Chemical Composition and Structure of the Cell Walls of the Conchocelis and Thallus Phases of *Porphyra Tenera* (Rhodophyceae)", J. Phycol. 17, 192–198 (1981).
Frazer et al., "Growth of the Conchocelis phase of *Porphyra Columbina* (Bangiales, Rhodophyta) at Different Temperatures and Levels of Light, Nitrogen and Phosphorus", Phycological Research, 43 249–253 (1995).
Chen et al., "Electrofusion of Protoplasts of Two Species of Porphyra (Rhodophyta)", Botanica Marina, 38 335–338 (1995).
Chen, "Protoplast Morphogenesis of *Porphyra leucosticta* in Culture", Botanica Marina, 30 399–403 (1987).
Fujita et al., "Isolation and Culture of Protoplasts from Some Seaweeds", Bulletin of Faculty of Fisheries, Nagasaki University, 57 (1985).
Fujita et al., "Protoplast Isolation and Fusion in Porphyra (Bangiales, Rhodophyta)", Hydrobiologia, 204/205 161–166 (1990).

(List continued on next page.)

*Primary Examiner*—Bruce R. Campell
*Assistant Examiner*—Anne Marie Grunberg
(74) *Attorney, Agent, or Firm*—Weingarten, Schurgin, Gagnebin & Lebovici LLP

(57) ABSTRACT

A method for the genetic modification and improvement of Porphyra species utilizing protoplast fusion is disclosed. The method of the invention features the use of conchoporangial branch conchocelis for at least one of the sources of protoplasts for protoplast fusion. Protoplasts produced from conchosporangial branch conchocelis of one species may be mixed with protoplasts produced from either blade material or conchocelis of a second species and fused using either a chemical fusing agent like polyethylene glycol (PEG) or electrofusion. Alternatively, an algal species other than a Porphyra species may be the second source of protoplasts. After fusion has occurred, fusion products are isolated and regenerated to whole plants or used as multicellular material. Because diploid conchocelis material is used as a source of protoplasts for at least one of the parents, regenerants can be produced that have stable, heritable, new genetic compositions, including hybrid, polyploid and aneuploid genomes, useful for strain improvement in the genus Porphyra.

11 Claims, 7 Drawing Sheets

PUBLICATIONS

Chen et al., "Protoplast Production From *Porphyra linearis* Using a Simplified Agarase Procedure Capable of Commercial Application", Journal of Applied Phycology, 6 35–39 (1994).

Shin et al., "Estimation of the Degree of Self-fertilizaion in *Porphyra yezoensis* (Bangiales, Rhodophyta)", Hydrobiologia, 204/205 397–400 (1990).

Miura et al., "Mendelian Inheritance of Pigmentation Mutant Types in *Porphyra yezoensis* (Bangiaceae, Rhodophyta)", Jpn. J. Phycol., 42 83–101 (1994).

Mizukami et al., "Effects of Cell Wall–lytic Enzymes on the Electrofusion Efficiency of Protoplasts from *Porphyra yezoensis*", Aquaculture, 108 193–205 (1992).

Mizukami et al., "Culture and Development of Electrically Fused Protoplasts from Red Marine Algae, *Porphyra yezoensis* and *P. suborbiculata*", Aquaculture, 132 361–367 (1995).

Polne–Fuller et al., "Developmental Studies in Porphyra. I. Blade Differentiation in *Porphyra Perforata* as Expressed by Morphology, Enzymatic Digestion, and Protoplast Regeneration", J. Phycol., 20 609–616 (1984).

Aguirre–Lipperheide et al., "Facts, Problems, and Needs in Seaweed Tissue Culture: An Appraisal", J. Phycol., 31 677–688 (1995).

Gall et al., "Isolation and Regeneration of Protoplasts from *Porphyra dentata* and *Porphyra crispata*", Eur. J. Phycol., 28 277–283 (1993).

Fujita et al., "Fusion of Protoplasts from Thalli of Two Different Color Types in *Porphyra yezonsis* Ueda and Development of Fusion Products", Jap. J. Physiol 35: 201–208 (1987).

Waaland et al., "Porphyra protoplasts: Isolation and Development", Journal Unknown, (1990).

Life history of the commercial species Porphyra yezoensis or P. tenera
(From Mumford & Miura, 1988)

1

2
40x

3

4
40x

5

STRAIN MANIPULATION AND IMPROVEMENT IN THE EDIBLE SEAWEED PORPHYRA

CROSS REFERENCE TO RELATED APPLICATIONS

This application claims priority from U.S. Provisional Application No. 60/069,563, filed Dec. 12, 1997, the whole of which is hereby incorporated by reference herein.

STATEMENT REGARDING FEDERALLY SPONSORED RESEARCH OR DEVELOPMENT

Part of the work leading to this invention was carried out with United States government support provided under a National Sea Grant Enhancement Grant entitled "Developing a commmercially viable seaweed aquaculture industry in New England." Therefore, the U.S. government has certain rights in this invention.

BACKGROUND OF THE INVENTION

The red alga Porphyra, or nori as it is commonly called, is the most widely eaten and commercially valuable seaweed in the world. Porphyra's main use is as the purple-black wrapping around the delicacy known as "sushi." Nori is commercially grown in Japan, China, Korea and Taiwan, and over 45,000 dry metric tons of nori are produced annually, worth over $2 billion US dollars. Because of its high protein and vitamin content, nori is considered to be a valuable health food. The market for nori sheets in the US alone is estimated to be worth at least $50 million dollars annually and is growing at a rate of over 17% per year. In addition, certain species of Porphyra also serve as important commercial sources of the red pigment r-phycoerythrin, which is utilized as a fluorescent "tag" for immunofluorescent studies and can cost as much as $360 per mg.

There are thought to be approximately 70 species of Porphyra worldwide, the majority of which are found in the North Pacific Ocean; approximately 33 species of Porphyra occur in Japan alone. Nori cultivation is a well developed industry, particularly in Japan where it has undergone significant technical improvements since the 1960's. Improvements made to the technical aspects of nori cultivation include the development of techniques for controlled culturing of its conchocelis stage in shells and for artificial seeding of spores produced by the conchocelis onto cultivation nets which can be stored until placed in the ocean.

As has been demonstrated repeatedly with agricultural crops and other types of cultivation, genetic improvement of cultured species is generally crucial for maximizing yield and developing cost-effective cultivation programs. Seaweeds, including Porphyra, are no exception. However, unlike land plants, seaweed strain improvement techniques have generally been restricted to classical breeding methods, particularly strain selection.

As a result of strain selection efforts, today there are several dozen cultivars of two Porphyra species, *P. yezoensis* and *P. tenera*, farmed in Japan. These cultivars were developed primarily as a result of the intensive strain selection program in Japan. Over many years of repeated selection, improvements were made in increasing the average length of fronds, as well as the length of the growing seasons of these two species (see Patwary and van der Meer, 1992). By comparison, efforts to develop new Porphyra strains through sexual hybridization have been far less successful. Intra- and interspecific crosses have been attempted in Porphyra but have contributed little (Suto, 1963). Often the products of sexual crosses have exhibited abnormal growth or chimeric (i.e., sectored) blades. In addition, because most commercially valuable species are monoecious, and thus easily self-fertilized, it is difficult in Poryhrya to produce F1 progeny of specific parents by sexual hybridization.

Thus, the most successful method of producing new strains of Porphyra to date has been through repeated strain selection. However, this approach has a number of disadvantages and limitations. In particular, repeated strain selection usually requires many years of intensive effort and is very labor intensive. In addition, the existing genetic variability in one or more populations of interest may not be sufficient for strain selection purposes. Furthermore, desirable and agronomically-beneficial traits that may be found in other species can not be taken advantage of by applying the methods that have been used in Porphyra in the past. Future improvements in the production of nori, both within and outside of the United States, will therefore most likely depend on the production of new strains that will have to be developed by new strain improvement methods.

One method of strain improvement that permits the rapid development of new strains and the transfer of genes and traits between species is somatic hybridization via protoplast fusion. Protoplast fusion is a well-developed technique in land plants and is just beginning to be successfully applied to seaweeds. In this technique, protoplasts are produced by enzymatically removing the cell walls that surround plant cells, and the protoplasts are then fused together to form a hybrid or a cybrid (i.e., cytoplasmic hybrid). Protoplast fusion can also be used to produce a polyploid or aneuploid. Like sexual hybrids, somatic hybrids generally exhibit combinations of traits found in the two parental plants hybridized. One major advantage of protoplast fusion is that it provides the opportunity to produce unique genomic combinations which are impossible or impractical by sexual hybridization, such as hybridizing individuals of different species and producing cybrids. Protoplast fusion has been reported in only a small number of seaweeds to date, including the green algae Ulva and Enteromorpha (Reddy et al. 1992) and the red algae Gracilaria (Cheney, 1990; Cheney and Duke, 1995), and Porphyra (e.g., Fujita and Migita, 1987; Fujita and Saito, 1990).

Efforts at protoplast fusion in Porphyra date back to 1986, when Saga et al. attempted to fuse protoplasts of a Porphyra species with those of the green alga Enteromorpha without success. Later, Fujita and Migita (1987) reported successfully fusing protoplasts of a wild type strain and a green mutant strain of *P. yezoensis* using the chemical fusagen polyethylene glycol (PEG). However, although they observed fusion and heterokaryon formation, they ultimately were able to produce only chimeric fronds which in turn produced greenish conchocelis that gave rise to green F1 fronds. In 1990, Fujita and Saito used both PEG and electrofusion techniques in fusion efforts with protoplasts from several Porphyra species. Similarly, Araki and Morishita (1990) attempted to fuse protoplasts between *P. yezoensis* and *P. tenera*. Mizukami et al. (1995) used electrofusion to fuse protoplasts between *P. yezoensis* and *P. suborbiculate* and report producing "hybrid-like" thalli. However, none of the fusion studies to date on Porphyra have resulted in a consistent reproducible technique that produces Porphyra strains with stable, improved properties. Effective and practical protoplast fusion methods that can be used for strain improvement in Porphyra would, therefore, be highly desirable.

BRIEF SUMMARY OF THE INVENTION

This invention is directed to a new method for producing wall-less cells, or protoplasts, from the commercially valuable edible seaweed Porphyra (also known as nori) and the use of protoplast fusion techniques for the production of new and improved strains of the same.

The method of the invention features the use of conchosporangial branch conchocelis for at least one of the sources of protoplasts for protoplast fusion. Protoplasts produced from conchosporangial branch conchocelis of one Porphyra species may be mixed with protoplasts produced from blade material, conchocelis or conchospores of a second Porphyra species and fused using, e.g., a chemical fusing agent like polyethylene glycol (PEG) or electrofusion. Other possible fusogens include sodium nitrate, dextran, high pH-high calcium containing solutions or combinations thereof. After fusion has occurred, fusion products are isolated, cultured to multicellular material and regenerated to whole plants. Alternatively, the multicellular material can be used as an undifferentiated cell mass.

Hybrids produced by the method of the invention are expected to possess combinations of the genetic material found in their respective parental species, and, therefore, are expected to exhibit combinations of their traits. Polyploids and aneuploids produced by the method of invention are expected to have one or more extra chromosome in their genome, and, therefore, to have present one or more extra copies of a gene that may code for a desirable trait.

The method of the invention includes a number of improvements over the prior art, which allow for protoplast fusion to be applied to Porphyra in a reproducible and controllable manner and which can result in products that were not possible to produce by prior art methods. For example, the use of conchosporangial branch conchocelis as a source of protoplast for protoplasts fusion simplifies the experiment process as the conchosporangial branch conchocelis phase is easier to grow, subculture and maintain contaminant-free in the laboratory than the blade phase. The term "conchosporangial branch conchocelis protoplasts" is defined here to mean protoplasts derived from conchocelis that bear conchosporangial cells. The term "protoplast" refers to a cell in which the cell wall has been enzymatically removed.

We have found that protoplasts produced from conchosporangial branch conchocelis can be fused with protoplasts produced from conchosporangial branch conchocelis of another species, as well as with protoplasts produced from the blades or thallus of another species. Furthermore, we have found that our method produces fusion products that have a higher capacity to regenerate to whole plants than blade-blade protoplast fusion products. In addition, fusion products produced by our method only infrequently result in chimeric blade formation, which is a common occurrence in blade-blade protoplast fusion.

The use of conchosporangial branch conchocelis material as a source of protoplasts for at least one of the parents means that regenerants can be produced that have stable, heritable, new genetic compositions, including hybrid, cybrid, polyploid and aneuploid genomes, useful for strain improvement in the genus Porphyra. Using the method of the invention, we have produced to date several unique plants that show one or more of the following features: 1) unique combinations of plant shape and color; 2) unique combinations of isoenzyme genetic markers; and 3) unique numbers of chromosomes or DNA contents. These plants may be either hybrids, cybrids, polyploids or aneuploids; any of these examples could represent an improved strain. Because both polyploids and hybrids in particular have been shown to be valuable cultivars for many land crop species, this discovery provides support for our methods for protoplast fusion being a useful and practical approach for strain improvement in Porphyra.

Therefore, the invention also features new varieties of Porphyra produced according to the method of the invention. In particular, the invention is directed to a variety of Porphyra, having the nuclear 18s rDNA sequence of *P. yezoensis* as found in GenBank Accession No. D79976, and furthermore having 4 or more chromosomes, preferably 4–6 chromosomes, (haploid number) per cell; or to a variety of Porphyra, having the nuclear 18s rDNA sequence of *P. umbilicalis* as found in GenBank Accession No. L36049, and furthermore having 5 or more chromosomes, preferably 5–8 chromosomes, (haploid number) per cell.

In addition, the invention is directed to a variety of a Porphyra species, selected from the group consisting of a variety having the nuclear 18s rDNA sequence of *P. haitanensis* and having 6 or more chromosomes (haploid number) per cell, a variety having the nuclear 18s rDNA sequence of *P. kuniedae* and having 3 or more chromosomes (haploid number) per cell, a variety having the nuclear 18s rDNA sequence of *P. leucosticta* and having 5 or more chromosomes (haploid number) per cell, a variety having the nuclear 18s rDNA sequence of *P. linearis* and having 5 or more chromosomes (haploid number) per cell, a variety having the nuclear 18s rDNA sequence of *P. pseudolinearis* and having 5 or more chromosomes (haploid number) per cell, a variety having the nuclear 18srDNA sequence of *P. purpurea* and having 6 or more chromosomes (haploid number) per cell, a variety having the nuclear 18srDNA sequence of *P. suborbiculata* and having 3 or more chromosomes (haploid number) per cell, and a variety having the nuclear 18srDNA sequence of *P. tenera* and having 4 or more chromosomes (haploid number) per cell.

DESCRIPTIONS OF THE DRAWINGS

Other features and advantages of the invention will be apparent from the following description of the preferred embodiments thereof and from the claims, taken in conjunction with the accompanying drawings, in which:

DETAILED DESCRIPTION OF THE INVENTION

Figure 1:
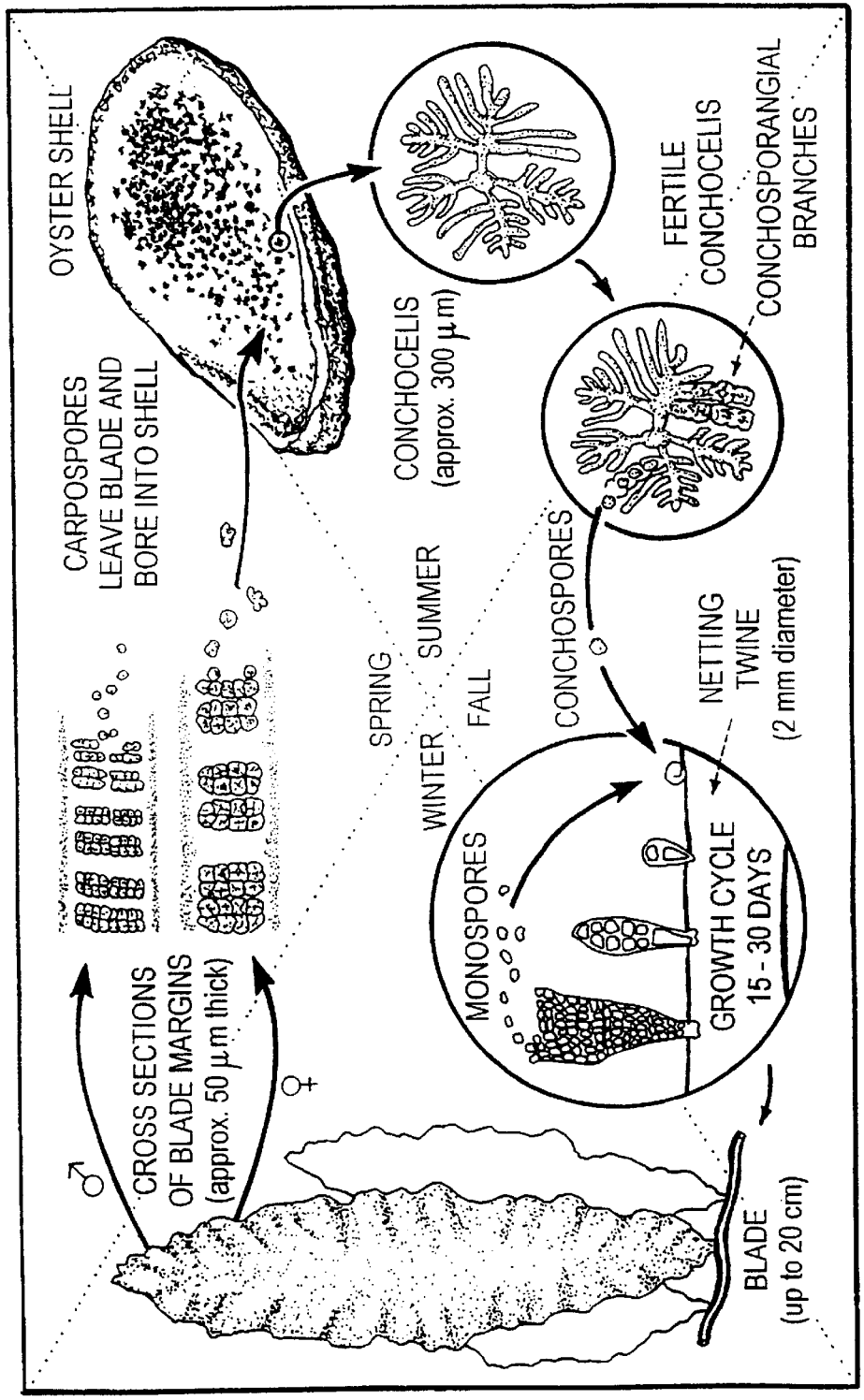
FIG. 1 is an illustration from a prior art reference of the life cycle of Porphyra sp. (Mumford and Miura, 1988)

The genus Porphyra has a biphasic life cycle, as shown in FIG. 1, that alternates between a macroscopic, haploid, gametophytic blade and microscopic, shell-boring, diploid, sporophytic filaments referred to as the "conchocelis" phase. Prior to 1949, the two parts of the life cycle were believed to belong to different genera of red algae, with the filamentous phase assigned to the genus Conchocelis. The gametophytic or blade phase is what is normally found in nature and is also what is grown on nets in nori cultivation. The haploid gametophytic phase consists of a membranous blade that may be one or two cells thick and either dioecious or monoecious, depending upon the species. In monoecious species, various sized blocks of male and female cells develop along the blade at maturity.

After sexual fertilization, diploid carpospores are produced by the blade, which give rise to the diploid sporophytic conchocelis phase. The gametophytic blade phase is seasonal and normally degenerates and dies after the production of carpospores. The sporophytic conchocelis phase produced by the carpospore typically grows as a mass of thin filaments embedded in shell and is difficult to observe in nature. The filaments are composed of very long cells with a very narrow diameter, typically around 3–10 $\mu$m wide and several times that in length.

Seasonal changes in environmental conditions induce the conchocelis to produce packets or branches of larger-sized cells, typically 15–25 $\mu$m in diameter, called conchosporangial branches, which, when mature, release diploid conchospores. Although there has been some controversy over the site of meiosis in the life cycle of Prophyra, it is generally accepted today that meiosis typically occurs during conchospore germination. That is, meiosis is generally thought to occur in the germinating conchospore such that the four initial cells of the new blade constitute the meiotic tetrad. The top three cells of this tetrad then divide further, giving rise to the bulk of the gametophytic blade, while the bottom cell divides a lesser amount and gives rise to a small rhizoidal holdfast.

Connecting the conchocelis phase with the blade phase of the Porphyra life cycle was crucial to the development of modern nori farming techniques. Today, typically, conchocelis cultures are grown on shells in large raceway tanks. They are induced to produce and release conchospores prior to the farming season through an alteration in light and temperature conditions. The conchospores released by the conchocelis are used to seed the nets that will be put out into the ocean to grow the blades, which are later harvested, dried and sold as nori sheets.

Figure 2:
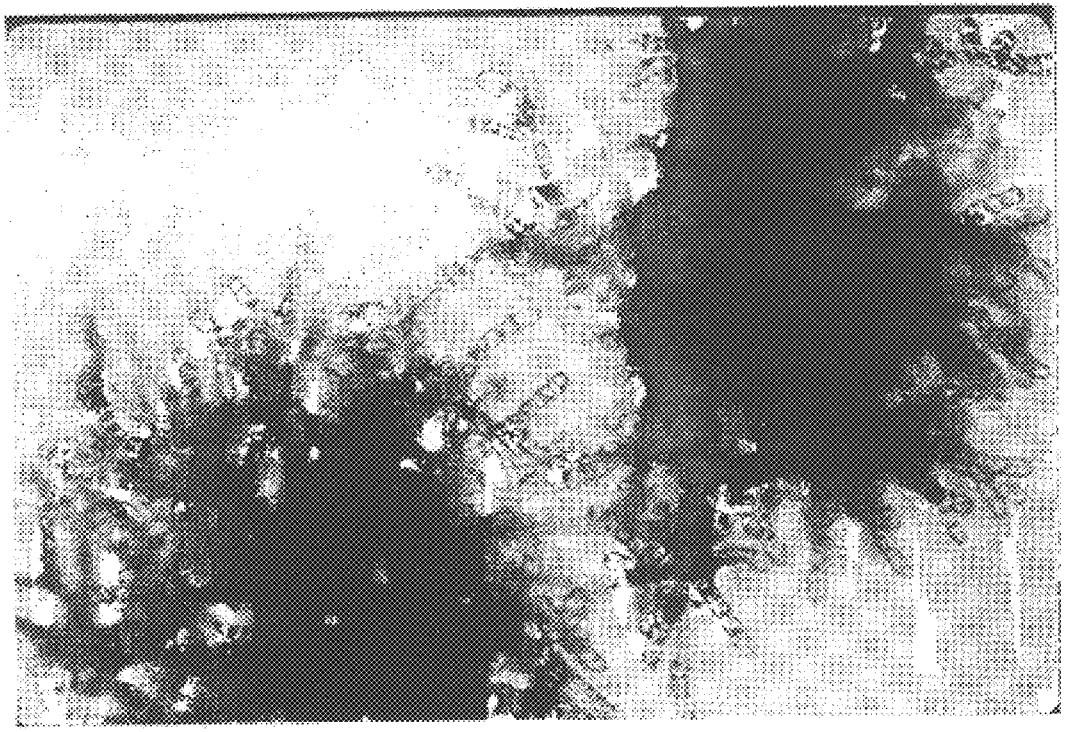
FIG. 2 shows an example of the morphology of conchosporangial branch conchocelis of Porphyra.

The principal feature of the method of the invention for protoplast fusion is its use of protoplasts produced from stabilized conchosporangial branches of the conchocelis phase of Porphyra. There are no previous reports of the use of conchosporangial branch conchocelis for producing protoplasts for protoplast fusion in Porphyra. The traditional source of material used to produce protoplasts for fusion in Porphyra has been the haploid blade phase of the Porphyra life cycle (e.g., Fujita and Migita, 1987; Fujita and Saito, 1990; Mizukami et al., 1992). In contrast, we utilize stabilized conchosporangial branch conchocelis (as shown in FIG. 2) to produce protoplasts. Conchosporangial branch conchocelis cells are very different in size and nature from the "vegetative" conchocelis filament cells. Typically, conchosporangial branch cells are much larger in diameter and much more cytoplasmically rich than the cells of "vegetative" conchocelis. Conchosporangial branch cells are typically not much longer than wide and are about 15–25 $\mu$m in diameter. In addition, their greater cytoplasmic density and smaller vacuole size make them a particularly appropriate source of protoplasts for protoplast fusion.

The use of the conchosporangial stage of conchocelis as a source of protoplasts offers a number of advantages for protoplast fusion in Porphyra over the traditional method. First of all, the conchosporangial conchocelis phase is easier to grow, subculture and maintain contaminant-free in the laboratory than the blade phase. Secondly, and more importantly, the general lack of success in Porphyra protoplast fusion appears to be connected to the unique way in which meiosis occurs in Porphyra. That is, as described above, meiosis occurs during the first two divisions of the germinating conchospore. Thus, by fusing protoplasts produced from haploid blades, past researchers were in effect always limited to initially producing a diploid product, which after meiosis and segregation produced a haploid and chimeric blade or thallus. In contrast, our use of diploid phase conchocelis for the production of protoplasts provides the advantage that we can produce triploid and tetraploid fusion products (depending on the ploidy of the other partner in the fusion). Thus, this approach provides the opportunity to produce polyploids and aneuploids as well as hybrids and cybrids; polyploids and hybrids in particular have been shown to be beneficial in land plant improvement. Secondly, we do not use the typical, thin conchocelis filaments that initially form from carpospores produced by blades, but instead use a stabilized and relatively rapidly growing free-living culture of conchosporangial branch filaments. The term "conchosporangial branch conchocelis" refers to cells of conchocelis that are in a pre-conchospore development phase. These cells are large, cytoplasmically-rich and ideal for fusion. In addition, conchosporangial branch conchocelis can be maintained in culture, particularly in free-living culture, to provide a constant and reliable source of contaminant-free protoplasts. We have found that protoplasts derived from conchosporangial branch conchocelis possess generally consistently high regeneration capability that is lacking in protoplasts produced from some Porphyra blades. We have been able to maintain and continuously grow these filaments without their becoming reproductive for over two years, using the methods of the invention.

Using our protoplast fusion method, we have produced several unique Porphyra plants. These plants show one or more of the following unique features: 1) unique combinations of plant shape and color, 2) unique combinations of isoenzyme genetic markers, and 3) unique numbers of chromosomes or DNA contents. One plant produced so far, for example, has the blade morphology and color of P. yezoensis, but a chromosome number of 6. This is unusual, since P. yezoensis blades are reported to have only 3 chromosomes (see, e.g., Cole, 1990). This plant may be either a hybrid, a cybrid or a polyploid; in any case it would be an improved strain. Polyploids, for example, produced in land plants often exhibit improved growth rates. So far, this plant has exhibited a faster growth rate than that of normal P. yezoensis in laboratory culture. Therefore, by providing a practical way to produce in Porphyra sp. the polyploids, cybrids and hybrids shown to be valuable cultivars for land crop species, the method of protoplast fusion according to the invention is a useful and practical approach for strain improvement in Porphyra.

Protoplast fusion is commonly accomplished by using one of two techniques; that is, by using either a chemical fusant, such as polyethylene glycol (PEG), or by electrofusion. Here we utilize the chemical fusant PEG, however, electrofusion should work equally well. There is considerable information available in the literature describing the specific details on the application of electrofusion to Porphyra (e.g., Mizukami et al., 1992; Mizukami et al., 1993; Mizukami et al., 1995; Chen et al., 1995).

Protoplast fusion should commence immediately after protoplasts have been isolated and washed. It is necessary to carry out the steps of protoplast fusion as quickly as possible, since Porphyra protoplasts begin producing a cell wall shortly (within hours) after they have been produced.

The parental species selected for fusion are chosen on the basis of a trait or traits they possess which would be advantageous or commercially-desirable to combine, or transfer, from one species to the other. As has been shown in land plants, it is possible to fuse protoplasts between plants that are intraspecific, interspecific (but intrageneric), and even intergeneric. We believe that protoplasts produced according to the method of the invention behave similarly. Thus, the two parental plants used with our invention do not have to belong to the same species, nor even to the same genus. One can select two different species for hybridization, e.g., one species having desirable cultivation properties under one set of conditions and the other species having desirable cultivation properties under a different set of conditions.

As an example of such a hybridization, we have carried out a number of protoplast fusion experiments using our method between a Porphyra species widely cultivated in Japan, *P. yezoensis*, and *P. umbilicalis*, a Porphyra species native to the North Atlantic Ocean and common along the coastline of northern Maine where it is intended that such a hybrid would be farmed. An example of a protoplast fusion experiment between these two species is described in detail below. Examples of product plants produced by such experiments are also described below. Similar experiments have also been conducted between *P. yezoensis* and *P. purpurea*, a second species native to the North Atlantic ocean. Other commercially useful Porphyra sp. from which protoplasts can be derived for practice of the method of the invention include *P. haitanensis, P. kuniedae, P. leucosticta, P. linearis, P. pseudolinearis, P. purpurea, P. suborbiculata,* and *P. tenera*.

In addition to selecting the two parental species based upon the desirable commercial traits they possess, consideration should be given to whether the candidate parental species have any particular traits that would facilitate hybrid selection after fusion. One such trait is differential pigmentation. It is important in a somatic hybridization experiment to have some mechanism by which heterokaryon fusion products can be distinguished and isolated from homokaryon fusion products and unfused cells following protoplast fusion. The products of our method of protoplast fusion are usually larger in size and differently pigmented from unfused, parental protoplasts. They also tend to be larger in size and/or differently pigmented from homokaryon fusion products. This makes the products of our method relatively easy to identify and isolate.

The method of protoplast fusion according to the invention is both reproducible and easily learned by those familiar with the art. Successful fusion experiments have been carried out by several different people in our laboratory. Plants have been produced by us that are different from their parental species, as well as different from each other. Thalli produced by our method are generally not chimeric and represent stable, heritable entities, whose traits can be passed on to their progeny. We have produced plants that differ from their parental strains in: morphology, pigmentation, isoenzyme pattern, chromosome number, and DNA content. Plants were analyzed electrophoretically for their phosphoglucose isomerase (PGI) pattern because the latter has been shown to be a reliable genetic marker for distinguishing Porphyra species (Watson et al., in press).

DNA content was quantified using a DNA-localizing fluorochrome and microspectrophotometric techniques similiar to those described in Kapraun et al (1991). The benefit of this latter technique is that it allows for the DNA content of individual cells to be determined. By measuring several cells throughout a blade by this method, one can determine whether or not a blade is a chimera.

Plants produced by the method of the invention are not sterile, but are reproductive and have the reproductive traits suitable for commercial cultivation. One plant, for example, has already been shown to have excellent conchocelis culture characteristics, as well as excellent conchospore and monospore release and net seeding capability.

In general, protoplast fusion according to the invention offers a number of advantages for strain improvement. For example, protoplast fusion as conducted here can be used to produce somatic (or parasexual) hybrids between species that are difficult or impossible to cross sexually; protoplast fusion can be used to produce somatic hybrids between species where one or both strains are sterile or between plant tissues that are not sexually reproductive; protoplast fusion can be used to produce asymetric hybrids, which contain all of the chromosomes of one parent and only some of the other; protoplast fusion can be used to produce cytoplasmic hybrids or cybrids; and protoplast fusion can be used to produce strains with altered chromosomal compositions, such as polyploid and aneuploid entities.

Furthermore, protoplast fusion according to the invention can be used to transfer polygenic traits from one species to another, closely related species (see Waara and Glimelius, 1995). This is a distinct advantage over the use of genetic engineering technology, where typically only single genes can be introduced into a species.

Some examples of specific applications of our invention for the improvement of Porphyra include (but are not limited to) the following:

1. Modifications to a species' growth characteristics by protoplast fusion with a second species that has, for example, different temperature tolerances, different nutrient requirements, and/or different light intensity sensitivities.
2. Improvements to a species' growth rate by using our invention to produce an interspecific hybrid, or intraspecific polyploid or aneuploid strain.
3. Modifications to a species' pigmentation composition by using our invention to produce an interspecific hybrid, or intraspecific polyploid or aneuploid strain.
4. Improvement to a species' tolerance to a disease, like that caused by Pythium, by protoplast fusion with another species with enhanced disease resistance. The species used for transferring disease resistance traits may or may not belong to the genus Porphyra. The source of disease resistance, for example, be a species of another algal genus, such as Ulva and Monostroma.
5. Modifications to a species' salinity tolerance by protoplast fusion with, for example, another species of lower or higher salintiy tolerance. The species used for transferring salinity tolerance traits may or may not belong to the genus Porphyra. The second species, for example, may belong to be a low-salinity tolerant species of Bangia.
6. Modifications to a species' metabolite composition, including (but not limited to) its fatty acid composition and its free amino acid composition, by protoplast fusion with, for example, a second species. The second species may or may not belong to the genus Porphyra. Modifications to a species' fatty acid composition, such as for example, the eicosapentaenoic acid (EPA) and docosahexanenoic acid (DHA) content, may increase its nutritional and health benefits. Modifications to a species' free amino acid composition may improve its taste characteristics.

The following examples are presented to illustrate the advantages of the present invention and to assist one of ordinary skill in making and using the same. These examples are not intended in any way otherwise to limit the scope of the disclosure.

EXAMPLE I

Production and Maintenance of Conchosporangial Branch Conchocelis of Porphyra Conchosporangial branch conchocelis (illustrated in FIG. 2) is cultured from thin filament or "vegetative" conchocelis. A conchocelis culture may be started from a single carpospore of the desired Porphyra species. We start our conchocelis cultures of P. yezoensis in either an enriched seawater medium (like ESS) or an artificial seawater plus plant growth regulators (pgrs) medium (like ASP-12) under low light conditions (e.g., less than 25 $\mu$Einsteins) and a long day photoperiod, 14–16 hrs, at a temperature of around 14° C. (Culture media are described in Cheney and Duke, 1995). After the thin filament conchocelis culture is grown for several weeks, it can be moved to a temperature, light quality and photoperiod to induce the production of conchosporangial branches. Some branches may form without any change in culture conditions. The exact conditions needed to induce conchosporangial branch formation depend upon the species and have been described in some cases or can be determined experimentally (Dring, 1967; Frazer and Murray, 1995). Once the conchosporangial branches are formed, we manually separate filaments with conchosporangial branches and place them into the wells of a muti-well plate in ASP-12 plus pgrs medium. We prefer to use a six well plate to culture conchosporangial branch conchocelis, although other containers may also be used. After they have been isolated from thin filaments, the conchosporangial branch conchocelis filaments are cultured at different conditions from those for culturing thin filaments. The optimal conditions for conchosporangial branch conchocelis formation and culture depend upon the species but generally consist of a temperature that is above that used for normally growing thin filament "vegetative" conchocelis, and the photo period is generally long day. Conditions are maintained so as not to induce conchospore production and release. For P. yezoensis, we have found that conchosporangial branch conchocelis grows well at a temperature of between 20–24° C., a photoperiod of 14 hours of light, and at a low light intensity of around 8–20 $\mu$Einsteins. After 1–2 weeks of growth, we again separate the conchosporangial branch filaments from any thin filaments in our conchosporangial branch conchocelis cultures and put them into new wells. This is similar to subcloning in tissue culture and is repeated until the conchosporangial branch conchocelis culture consist of only conchosporangial branch filaments.

Such cultures can be maintained under these conditions indefinitely and thereby provide a constant, stabilized source of conchosporangial branch conchocelis for protoplast production. We change the culture medium of such cultures every 3–4 weeks to maintain the cultures and weekly just prior to protoplast isolation. In addition, good culture methods should be utilized during the isolation period and maintenance, such that the cultures are kept epoiphyte-free and essentially bacteria-free.

EXAMPLE II

Protoplast Production from Conchosporangial Branch Conchocelis

Although the cell wall composition of conchosporangial branch conchocelis in Porphyra is reported to be different from that of Porphyra blade cells (Mukai, et al, 1981), we have found that it can be digested using an enzyme mixture similiar to that we use for producing blade protoplasts. The preferred method for protoplast production in P. yezoensis conchosporangial branch conchocelis is shown in FIG. 4A, 1–5, and described below. However, these methods and conditions might have to be modified depending upon the species.

Figure 3:
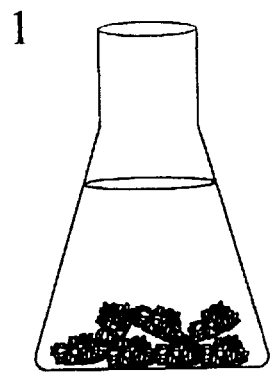
FIG. 3 shows production of conchosporangial branch conchocelis of Porphyra according to the method of the invention.
Figure 3:
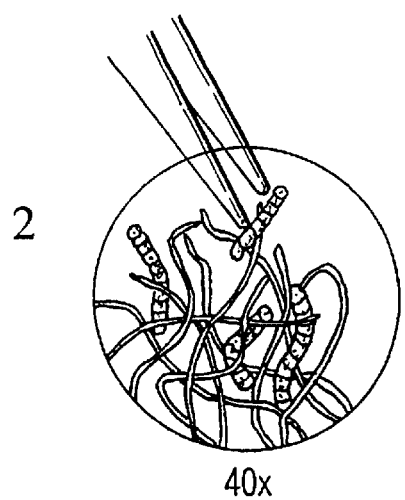
Figure 3:
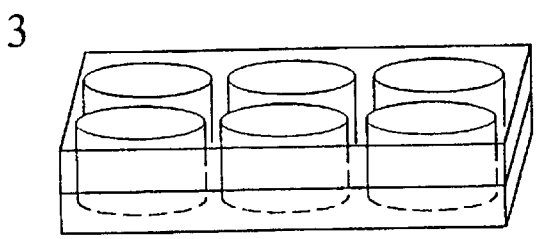
Figure 3:
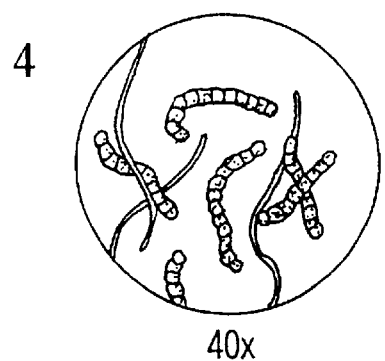
Figure 3:
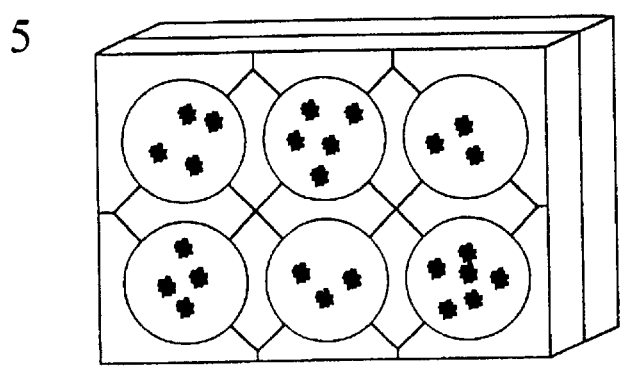
Figures 4A, 4B:
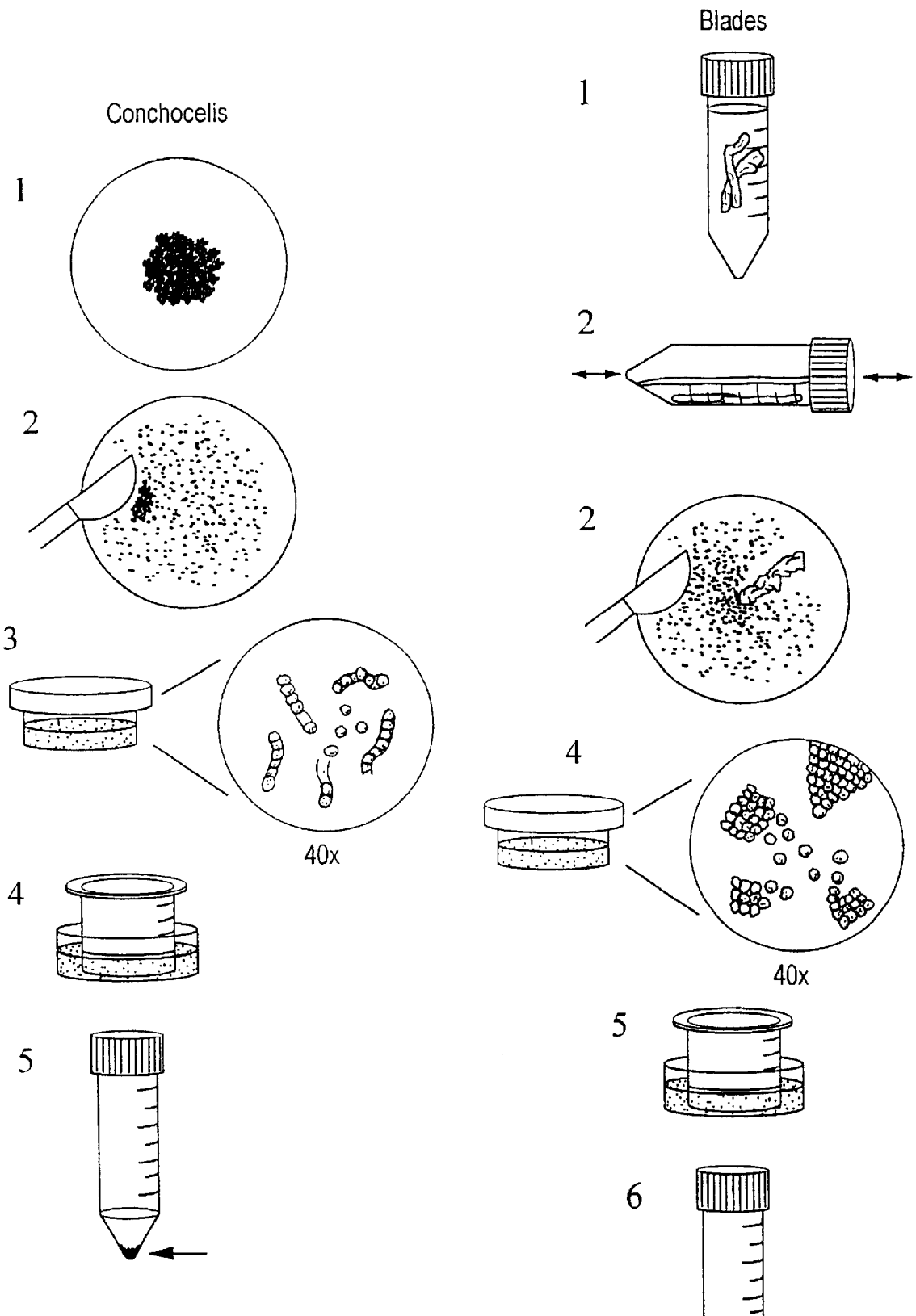
FIG. 4A shows protoplast production from conchosporangial branch conchocelis of Porphyra according to the method of the invention.
FIG. 4B shows protoplast production from blades of Porphyra.

One of the advantages of our invention is that contaminate-free conchosporangial branch conchocelis cultures can be maintained at a ready state for a protoplast fusion experiment with very little difficulty and labor. Typically, the only thing we do to pretreat the conchosporangial branch conchocelis for protoplast isolation is to change the medium weekly for one or two weeks to make certain the cells are healthy and darkly pigmented. The amount of conchosporangial branch conchocelis material required for a protoplast fusion experiment varies with the number of fusions being attempted. We typically use approximately 100 mg wt weight of material to perform between 8–12 fusions (FIG. 4A, 1). This material is finely chopped using a scalpel or razor blade (FIG. 4A, 2) and rinsed twice with a 0.5 M mannitol filtered seawater rinse medium. After rinsing, the chopped conchosporangial branch conchocelis is treated with a cell-wall digesting enzyme mixture for 1–1.5 hours typically, at a ratio of approximately 100 mg of tissue per 2.0 ml of enzyme solution (FIG. 4A, 3). The preferred enzyme mixture used to produce protoplasts consists of: 2% abalone acetone powder, 1% Onozuka RS cellulase and 50 $\mu$l $\beta$-agarase in a 0.5 M mannitol filtered seawater solution. Other enzyme mixtures have been reported for producing blade protoplasts in Porphyra, and these may also work for conchosporangial branch conchocelis. The particular enzyme mixture used should be selected on its ability to digest the cell wall without substantially and adversely affecting the viability and regeneration capability of the resultant protoplasts.

After protoplast release, the enzyme mixture is filtered through a 25 $\mu$m sterile mesh, and collected in a centrifuge tube. The protoplasts are then collected by gentle centrifugation (e.g., at 500–700 rpm). The supernatant is removed and the protoplasts are resuspended in a 0.5 M mannitol filtered seawater rinse medium. The rinse medium is adjusted to 1 ml and the protoplast yield is determined. Protoplasts can be stored on ice for a short period until protoplasts from both parental sources are ready for a fusion experiment.

EXAMPLE III

Protoplast Production from Blades

There are over 20 reports on protoplast isolation from Porphyra blades. The specific methods and enzyme mixtures used vary from species to species and author to author. However, in general similar methods are used throughout. The preferred method for P. yezoensis and P. umbilicalis blades is shown in FIG. 4B, 1–5, and described below. These methods and conditions might have to be modified depending upon the species. Also, as described below, it usually takes a longer time for blade protoplasts to be released than for conchosporangial branch conchocelis protoplasts; therefore, we typically start blade protoplast isolation procedures 1–2 hours before the conchosporangial branch isolation procedures so that both types of protoplasts will be ready for fusion at about the same time.

Blades used as a source of protoplasts should be carefully selected. They should be as healthy and actively growing as possible, as well as epiphyte free. We prefer to use freshly collected, young, actively growing blades. We have had mixed results using blades that were previously frozen. We have also found that blades maintained for a long time in laboratory culture do not provide a good source of protoplasts. Prior to protoplast treatment, blades should be cleaned of any obvious epiphytes and contaminants. One simple way to clean blades is to put them into a container of sterile seawater, such as a centrifuge tube (FIG. 4B, 1), and shake it vigorously for a couple of minutes, after which the seawater is removed and replaced. The procedure is repeated at least twice more or until the water appears clear.

After the blades have been cleaned, they are treated with a 10% papain filtered seawater solution for approximately 1 hr. We typically place them into a centrifuge tube held on a rotary shaker and shaken at 50–100 rpm. The amount of blade material required for a protoplast fusion experiment varies with the success of the protoplast isolation and the number of fusions being attempted. We typically use around 150–200 mg wt weight of material to perform between 8–12 fusions. After papain treatment, the blades are rinsed three times with filtered seawater and finely chopped using a scalpel or razor blade (FIG. 4B, 3) and rinsed twice with a 0.5 M mannitol filtered seawater rinse medium. After rinsing, the chopped blade material is treated with a cell-wall digesting enzyme mixture at a ratio of approximately 100 mg of tissue per 2.0 ml of enzyme solution (FIG. 4B, 4). The preferred enzyme mixture used to produce protoplasts from blades is the same as that used for conchosporangial branch conchocelis (i.e., 2% abalone acetone powder, 1% Onozuka RS cellulase and 50 μl β-agarase in a 0.5 M mannitol filtered seawater solution); however, the enzyme treatment is typically longer, lasting from 2–3 hours. The enzyme treatment is carried out in a small Nunc dish on a rotary shaker at 50–100 rpm at around 20–24° C. Other enzyme mixtures have been reported for producing blade protoplasts in Porphyra. After protoplast release, the enzyme mixture is filtered through a 25 μm sterile mesh (FIG. 4B, 5), and collected in a centrifuge tube. The protoplasts are then collected by gentle centrifugation (e.g., at 500–700 rpm). The supernatant is removed and the protoplasts are resuspended in a 0.5–0.7 M mannitol filtered seawater rinse medium. The rinse medium is adjusted to 1 ml (FIG. 4B, 6) and the protoplast yield is determined. Protoplasts can be stored on ice for a short period until protoplasts from both parental sources are ready for a fusion experiment.

EXAMPLE IV

Protoplast Fusion

An advantage of the method of the invention over the prior art is that at least one of the parental sources of protoplasts for protoplast fusion is conchosporangial branch conchocelis; the other parental source of protoplasts may be, e.g., either conchosporangial branch conchocelis or blade material. The protoplasts may be fused using either electrofusion or chemical fusion. Both methods of protoplast fusion have been used previously with Porphyra (e.g., see Fujita and Migita, 1987; Fujita and Saito, 1990; Mizukami et al, 1995). Here we describe details for chemical fusion, but electrofusion methods reported in the literature can also be applied.

In general, the fusion of protoplasts by chemical fusion is accomplished by treating the protoplasts with a chemical fusogen agent to cause them to agglutinate, treating the agglutinated protoplasts with a hypotonic fusion solution which is effective to cause them to fuse, replacing the fusion solution with a hypertonic washing solution to remove fusogen residues and provide a hypertonic environment, and finally replacing the washing solution with culture medium which is effective in stimulating cell wall formation and cell division. Examples of fusogens which may be expected to function in this invention include polyethylene glycol (PEG), sodium nitrate, dextran, high pH-high calcium containing solutions, and combinations of these. The preferred chemical fusogen is PEG.

Figure 5:
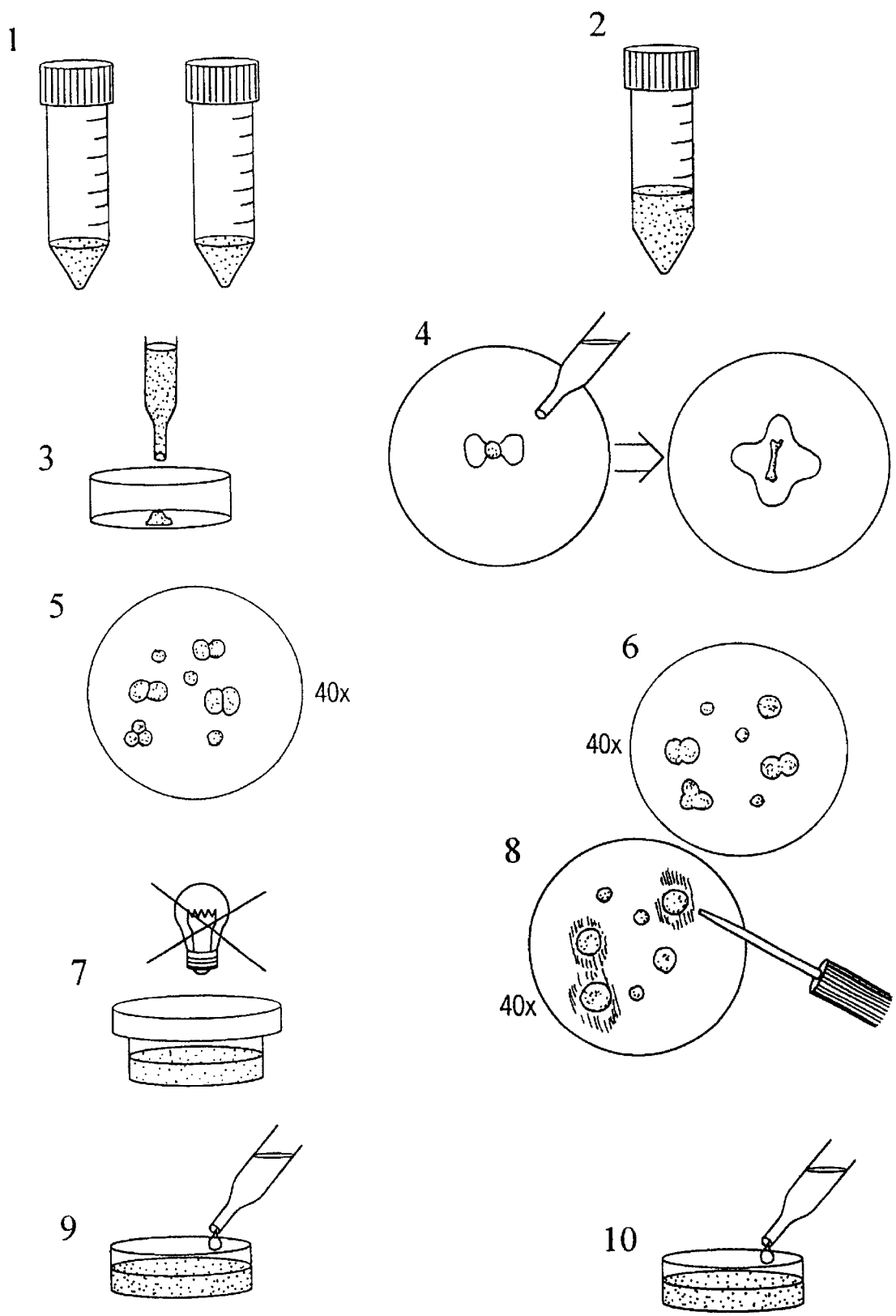
FIG. 5 shows protoplast fusion in Porphyra according to the method of the invention.
Figure 6A:
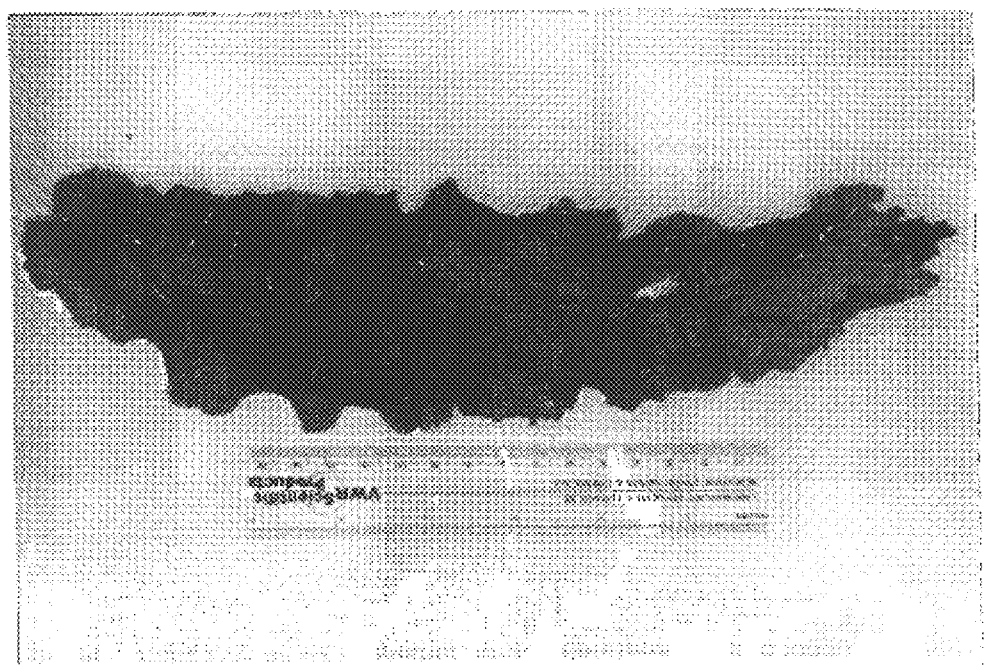
FIG. 6 shows the morphology of a novel variety of *P. yezoensis* produced according to the method of the invention.

The steps of protoplast fusion are illustrated in FIG. 5. All steps are conducted in a sterile hood. Protoplast fusion is initiated by combining equal numbers of protoplasts from the two parental sources into a single centrifuge tube (FIG. 5-1) and gently mixing them together. For best results, the combined concentration of protoplasts should be great enough to insure a close proximity of protoplasts in the "fusion drop." Satisfactory fusion rates can be obtained with combined protoplast densities in the range of $4-8\times10^4$ protoplasts per ml (FIG. 5-2). Next, typically one drop of the combined protoplast mixture is pipetted onto the center of a culture dish. The approximate number of protoplast in this so-called "fusion drop" should be around $2-4\times10^3$. If the protoplast density is below this, a second drop can be added on top of the first drop. The culture dish used can be a petri plate, but a small (3.5 cm diameter) Nunc dish with a coated surface is preferred. The fusion drop is left undisturbed for a brief period, usually 15–20 minutes, to allow the protoplasts to settle.

Next, four drops of a 50% PEG solution (made up in distilled or deionized water) are added to opposite sides of the "fusion drop" in the manner shown in FIG. 5-4. In the preferred method, a high molecular weight, low carbonyl content PEG is used such as Kochlight 6,000, Kochlight 8,000, or Aldrich 8,000. The PEG solution should be made up fresh just before use and filter sterilized. The mixture is left undisturbed for 10–20 minutes, or until protoplast agglutination and membrane compression have been observed FIG. 5-5). After this occurs, the PEG solution is carefully removed and replaced with 5–10 drops of a fusion solution that is hypotonic relative to the PEG solution. The preferred fusion solution consists of 0.5 M mannitol in filtered seawater. However, other fusion (or elution) solutions have been described that may also be used. The fusion solution is left undisturbed for 10–20 minutes or until cytoplasmic mixing has been observed between fusing protoplasts (FIG. 5-6). If fusions do not appear to be progressing satisfactorily, then it may be necessary to replace the fusion solution with 4–10 more new drops.

As soon as sufficient numbers of fusion products are observed, the fusion solution is removed and the Nunc dish is gently but quickly flooded with 1 ml of an initial culture medium, typically consisting of 0.7 M mannitol in filtered seawater. This solution is of a higher osmolarity than the fusion solution and is added to the edge of the Nunc dish in a manner that will not disturb the fusion products in the center of the dish. After the addition of the initial culture medium, the Nunc dishes are left undisturbed for 48 hours in generally low light—low temperature culture conditions. For *P. yezoensis*—*P. umbilicalis fusions*, the preferred initial culture conditions are a temperature of 14° C., and little (less than 8 µEinstein) or no light. The optimum temperature and light conditions for other fusions would depend on the species used. After 48 hours, the initial culture medium is diluted in a step-wise fashion by adding 10 drops (or 0.5 ml) of filtered seawater daily for 7 days. This reduces the mannitol concentration of the initial culture medium by 0.1 M daily until there is no more mannitol left in the culture medium. Once completely diluted, this medium is replaced with a final culture medium and the fusion products are cultured at a light level and temperature to promote cell wall formation and cell division. The optimal final culture medium and conditions may vary depending upon the species. The preferred final culture medium *P. yezonensis*—*P. umbilicalis* fusions is ESS/2, although an artificial culture medium, such as ASP-12 plus pgrs, can also be used. The preferred culture conditions are 14° C. and a light level of around 8–10 µEinsteins, with a 12:12 photoperiod. The culture medium is changed weekly by carefully removing and replacing 50% of its volume.

EXAMPLE V

Isolation and Culture of Protoplast Fusion Products

In any fusion experiment, it is important to have a reliable method for identifying and isolating those cells that are believed to be fusion products. For the purpose of this invention, we are interested in identifying both putative heterokaryon (i.e., biparental) and homokaryon (i.e., uniparental) fusion products, since the former may give rise to a hybrid or a cybrid (i.e., a cytoplasmic hybrid), and the latter may give rise to a polyploid or an aneuploid new strain. Various methods of identifying and selecting hybrids have been described in the literature (e.g., Waara and Glimelius, 1995) which can be applied to this invention.

One of the simplest methods for distinguishing heterokaryon and homokaryon fusion products from unfused protoplasts is the use of visual identification. This is made relatively easy in this invention because conchosporangial branch conchocelis protoplasts are typically more darkly pigmented and larger in size than blade protoplasts. Thus, fusion products produced by our method are typically larger in size and differently pigmented from unfused, parental protoplasts. While it is more difficult to distinguish heterokaryon from homokaryon fusion products, this can be done in cases involving conchocelis and blade fusions, since homokaryon conchocelis fusion products are typically larger in size and differently pigmented from homokaryon blade fusion products and from heterokaryon fusion products. This makes the products of our method generally easier to identify and isolate than those of the prior art.

Heterokaryon and homokaryon fusion products that can be visually distinguished, however, may lose their distinctive appearance within a relatively short period of time, for example, within a few days. Therefore, it is essential to isolate or "mark" these cells while they are still easily distinguished. One method that has been used to isolate fusion products in Porphyra in the past is simply to remove them from the unfused protoplasts with a micropipet and put them into a separate plate or dish (e.g., Fujita and Migita, 1987). The preferred method is not to remove them but rather to "mark" their exact location so that they can be identified at a later time. We believe it is beneficial to leave fusion products undisturbed until they are well attached to the bottom of the culture dish, which can take several days. It has been shown that it is essential for a protoplast to be attached to a surface in order for it to divide. Therefore, we "mark" the location of each putative heterokaryon or homokaryon fusion product by scratching the bottom of the culture dish around the fusion product with a micropipet or fine probe, as shown in FIG. 5-8. This process can typically be done 2–3 days after fusion, and as with all other fusion steps, should be carried out in a sterile hood.

Once the protoplast fusion products of interest have been "marked", they are cultured under conditions that should be optimal for cell division and growth. The exact conditions may depend upon the species involved. For *P. yezoensis* and *P. umbilicalis* protoplast fusion products, the preferred method is to culture them in an enriched seawater medium, like ESS/2, although an artificial culture medium, such as ASP-12 plus pgrs, can also be used. Antibiotics may be added to the culture medium if needed to control bacterial growth. However, any antibiotic solution should be pretested for its effects on protoplast growth. We have found that low concentrations of the several antibiotics (e.g., E3/2, Cheny and Duke, 1995) may be used for this purpose. The preferred culture conditions are 14° C., a light level that gradually increases over several weeks from around 8–10 µEinsteins to 20–25 µEinsteins, and a 12:12 or longer photoperiod. The culture medium is changed weekly by carefully removing and replacing 50% of its volume for the first 3–4 weeks (FIG. 5-9), and then replacing the entire volume after that (FIG. 5-10). Other culture conditions are also appropriate for this invention.

Fusion products are maintained in the conditions described above until they have developed into a multicellular stage, typically in the form of a small bladelet. At this point, they are removed from the Nunc dish either by micropipet, or, if large enough, by microforceps. The fusion products are transferred to a flask on a shaker or an aerated flask, whichever promotes their rapid development into whole plants. The preferred method is to use aerated, small flasks with gentle bubbling for the first two weeks, and then to increase the size of the flask and the intensity of the aeration as the blade gets bigger.

In order to determine the nature of the whole plant produced from the fusion product, the plant should be analyzed to determine if it is the product of a heterokaryon or homokaryon fusion, and whether it has the traits that were desired. In general, various methods have been used to analyze protoplast fusion products, including morphology, pigmentation, fatty acid composition, isoenzyme pattern, chromosome number, DNA content, and DNA probes. The details of such methods are described in the literature (e.g., see Waara and Glimelius, 1995, and papers cited therein; Kito et al., 1998; Watson et al., in press). We have used a combination of traits to distinguish fusion products of potential interest, including: blade shape and color, PGI isoenzyme electrophoretic banding pattern, chromosome number, DNA content, and DNA probes for 18srDNA and rbcL sequences. Using this combination of analyses, we have identified several new Porphyra strains that are different from their parental plants as well as each other. Six of these plants are described below.

EXAMPLE VI

Examples of Plants Produced by the Method of the Invention

1. #9-13

This plant was produced in a protoplast fusion experiment between conchosporangial branch conchocelis protoplasts from *P. yezoensis* (strain U-51) and blade protoplasts from the local species *P. umbilicalis*. Plant #9-13 has the morphology, color (FIGS. 6A and 6B) and PGI isoenzme pattern (FIG. 7) of *P. yezoensis* but has 6 chromosomes instead of the usual 3 chromosomes for *P. yezoensis*. It also has approximately twice as high DNA content as *P. yezoenis*. The nuclear 18sr DNA gene sequence of this isolate has been analyzed, and it appears to be identical to that of *P. yezoensis*. Therefore, we believe this plant to be a polyploid or a cybrid, although the possibility of its being a hybrid cannot be eliminated. This would be the first report of a polyploid, cybrid or hybrid being produced in Porphyra.

Figure 6B:
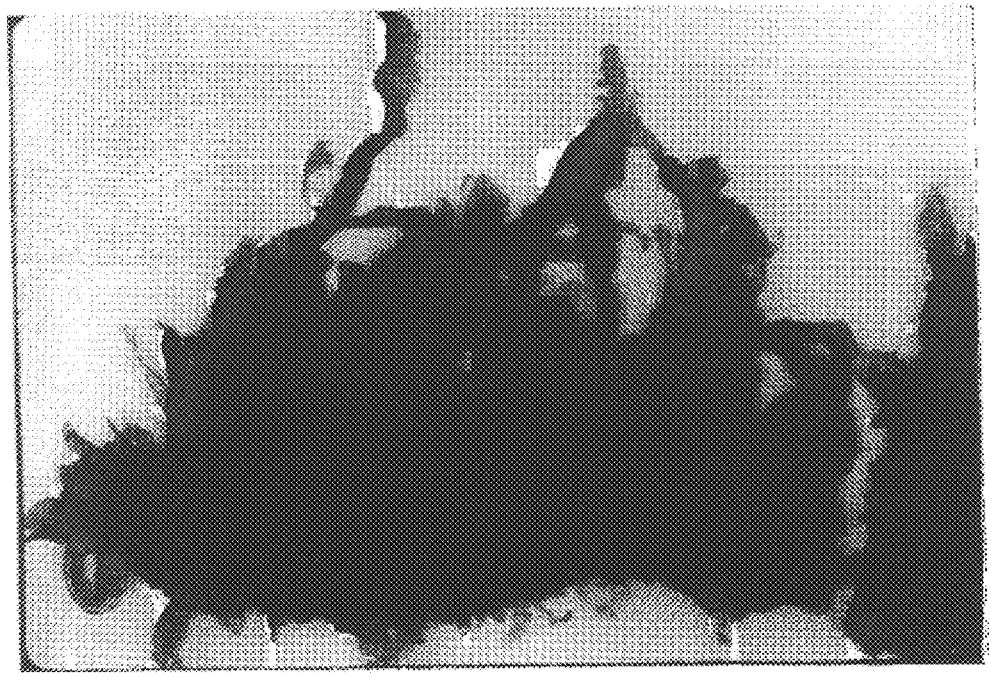
Figure 7:
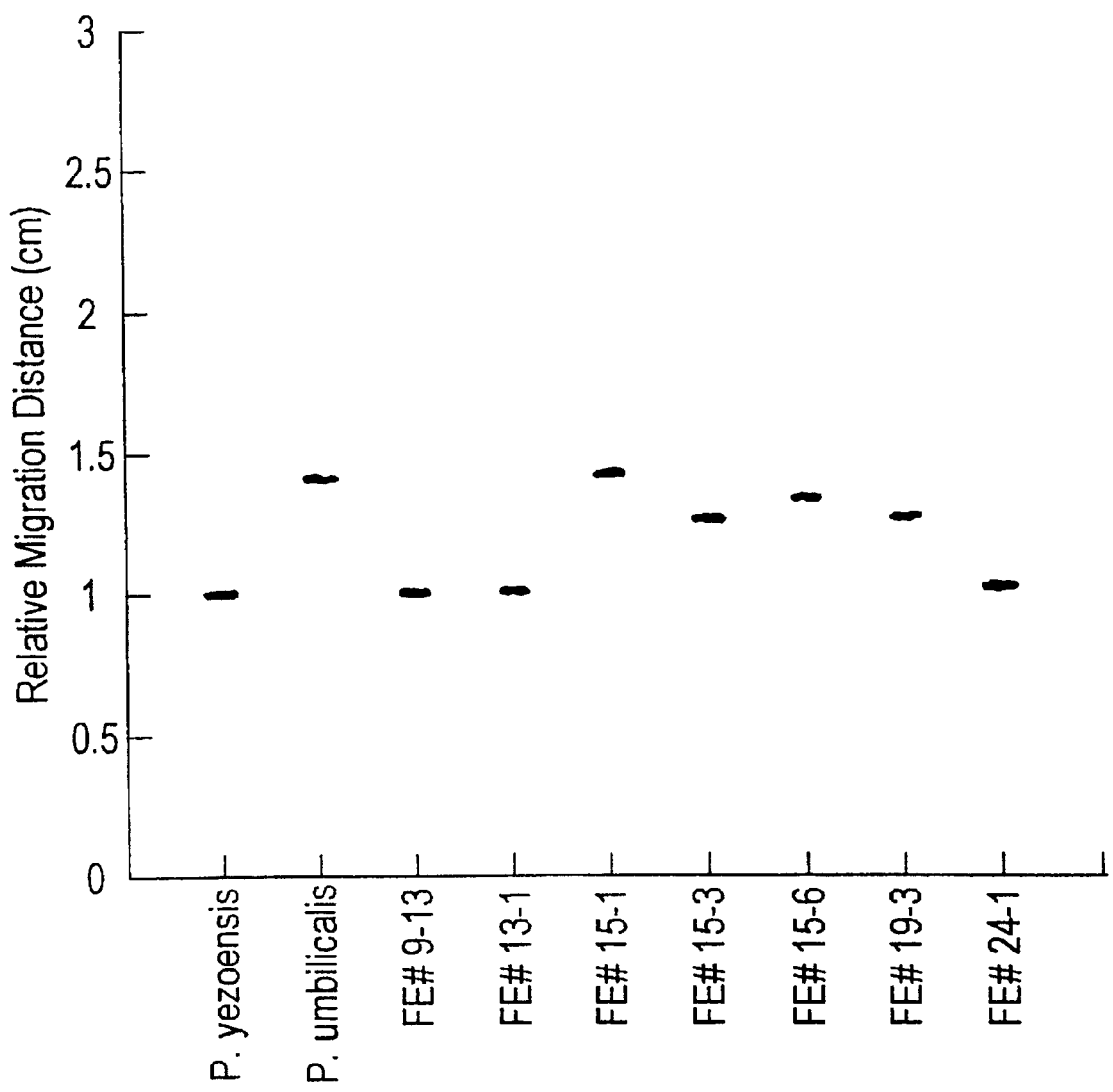
FIG. 7 is a graph showing electrophoretic banding patterns for phosphoglucose isomerase (PGI) from parental strains *P. yezoensis* and *P. umbilicalis* and from seven fusion product plants (migration distances are set relative to the *P. yezoensis* control).

9-13 has been shown to grow faster in laboratory culture conditions than P. yezoensis. Conchocelis from #9-13 has been seeded and grown on shells and induced to release conchospores to seed commercial nori nets, which have been successfully grown in the waters of northern Maine (FIG. 6B). Its conchospore and monospore release patterns are as good or better than strain U-51 plants, and its growth rate in northern Maine waters so far looks better than that of strain U-51.

2. #13-1

This plant was produced in a protoplast fusion experiment between conchosporangial branch conchocelis protoplasts from *P. yezoensis* (strain U-51) and blade protoplasts from the local species *P. umbilicalis*. Plant #13-1 has the morphology, color and PGI isoenzme pattern of *P. yezoenis* (FIG. 7) but has a higher DNA content value than that of *P. yezoensis* or new variety #9-13.

3. #15-3

This plant was produced in a protoplast fusion experiment between conchosporangial branch conchocelis protoplasts from *P. yezoensis* (strain U-51) and blade protoplasts from the local species *P. umbilicalis*. Plant #15-3 has the morphology and color of *P. umbilicalis*, but a PGI isoenzme pattern different from that of either parent (FIG. 7) and a DNA content value that is greater than either parental species.

4. #19-6

This plant was produced in a protoplast fusion experiment between conchosporangial branch conchocelis protoplasts from *P. yezoensis* (strain U-51) and blade protoplasts from the local species *P. umbilicalis*. Plant #15-6 has the morphology of *P. umbilicalis* but is darker purple in pigmentation. It also has a PGI isoenzme pattern different from that of either parent (FIG. 7) and a DNA content value that is greater than that of either parental species.

5. #19-3

This plant was produced in a protoplast fusion experiment between conchosporangial branch conchocelis protoplasts from *P. yezoensis* (strain U-51) and blade protoplasts from the local species *P. umbilicalis*. Plant #19-3 has the morphology of *P. umbilicalis*, but is lighter in pigmentation than *P. umbilicalis*. It also has a PGI isoenzme pattern different from that of either parent (FIG. 7) and a DNA content value that is greater than that of either parental species.

6. #24-1

This plant was produced in a protoplast fusion experiment between conchosporangial branch conchocelis protoplasts from *P. yezoensis* (strain U-51) and blade protoplasts from the local species *P. umbilicalis*. Plant #24.1 has the morphology and color of *P. umbilicalis*, but has a PGI isoenzme pattern similiar to that of *P. yezoensis* (FIG. 7) and a DNA content value that is greater than either parental species.

REFERENCES

Arkai, T and Morishitia T, 1990. Fusion of protoplasts from wild type *P. yezoensis* and green type *P. tenera* thalli (Rhodophyta). Nippon Suisan Gakkaishi 56:1161.

Chen, L., I. McCracken and Z. Xie, 1995. Electrofusion of protoplasts of two species of Porphyra. In: *Bot.Marina* 38: 335–338.

Cheney, D., 1990. Genetic improvement of seaweeds through protoplasts fusion. Economically important marine plants of the Atlantic, C. Yarish et al. (eds), Conn. Sea Grant College Program, pp 15–25.

Cheney, D., 1997. Strain improvement through protoplast fusion/somatic hybridization in commercial red seaweeds. In: *Phycoloqia* V. 36, Suppl. pg 18.

Cheney et al., 1998. Genetic manipulation and strain improvement of commercially valuable red seaweeds. In: *New Developments in Marine Biotechnology*, Y. LeGal and H Haluroson (ed.). Plenum Press, NY, pp 101–104.

Cheney, D. and C. Duke, 1995. U.S. Pat. No. 5,426,040. "Methods for producing improved strains of seaweed by fusion of spore-protoplasts, and resultant seaweeds and phycocolloids."

Cole, K., 1990. Chromosomes. In: *The biology of red algae*, K. Cole and R. Sheath (eds.), Cambridge Univ. Press, NY, pp 73–101.

Dring, M. 1967. Effects of day length on growth and reproduction of the conchocelis-phase of *P. tenera*. *J. Marine Biol*. Ass. U.K. 47:501–510.

Frazer, A. and Murray, T., 1995. Growth of the conchocelis phase of *Porphyra columbina* (Bangiales, Rhodophyta) at different temperatures and levels of light, nitrogen and phosphorus. In: *Phycological Research*, 43:249–253.

Fujiita, Y. and S. Migita, 1987. Fusion of protoplasts from thalli of two different color types in *Porphyra yezonsis* and development of fusion products. In: *Jan. J. Phycol*. 35: 201–208.

Fujita, Y. and M. Saito, 1990. Protoplast isolation and fusion in Porphyra (Bangiales, Rhodophyta). In: *Hydobiologia* 204/205: 161–166.

Kapraun, D., T. Hinson and A. Lemus, 1991. Karyology and cytophotometric estimation of inter- and intraspecific nuclear DNA variation in four species of Porphyra (Rhodophytra) *Phycoloqia*, 30: 458–466.

Kito, H., Kunimoto, M., Kamanishi, Y., and Mizukami, Y. 1998. Protoplast fusion between *Monostroma nitiduma* and *P. yezoensis* and subsequent growth of hybrid plants. *J. ApDlied Phycology* 10: 15–21.

Mizukami, Y., M. Okauchi and H. Kito, 1992. Effects of cell wall-lytic enzymes on the electrofusion efficiency of protoplasts from *Porphyra yezoensis*. Aquaculture 108: 193–205.

Mizukami, Y., H. Kito and M. Okauchi, 1993. Factors affecting the electrofusion efficiency of Porphyra protoplasts. In: *J. Applied Phycoloqy* 5:29–36.

Mizumkami, Y., Okauchi, M., Kito, S., Ishimoto, S., Ishida, T., and Fuseya, M. 1995. Culture and development of electrically fused protoplasts from red algae, *P. yezoensis* and *P. suborbiculata. Aguaculture* 132: 361–367.

Mukai, L., Craigie, J and Brown, R, 1981. Chemical composition and structure of the cell walls of the conchocelis and thallus phases of Porphyra Tenera (Rhodophyceae). In: *J. Phycol*. 17, 192–198.

Mumford, T., and Miura, A., 1988. Porphyra as food: cultivation and economics. In: *Algae and Human Affairs*. C. Lembi and J. R. Waoland (eds.), Cambridge Univ. Press, Cambridge, pp 87–117.

Patwary, M., and van der Meer, J., 1992. Genetics and breeding of cultivated seaweeds. In: *Korean J. Phycol*. 7:281–318.

Reddy, C. et al., 1992. Induction of fast growing and morphologically different strains through intergeneric protoplast fusions of Ulva and Enteromorpha. In: *J. of Applied Phycol.* 4: 57–65.

Saga, N., M. Polne-Fuller, and A. Gibor, 1986. Protoplasts from seaweeds: production and fusion. Beihefte zur Nova Hedwigia 83: 37–43.

Suto, S., 1963. Intrageneric and interspecific crossing of the lavers (Porphyra). In: *Bull. JaD. Soc. Sci. Fish.* 29: 739–748.

Waara, S. abd K. Glimelius, 1995. The potential of somatic hybridizaion in crop breeding. *Euphytica* 85: 217–233.

Watson, K., Cheney, D and Levine, U, 1999. Biomonitoring of an aquacultured introduced marine alga, *Porphyra yezoenisi* (Rodophyta, Bangiophycideae) in Eastport, Maine. J. Applied Phycology (in press).

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

What is claimed is:

1. A method for producing a new or modified strain of the red alga Porphyra, said method comprising the steps of:
    preparing first protoplasts from a stabilized culture of conchosporangial branch conchocelis of a first species of Porphyra;
    fusing said first protoplasts with second protoplasts selected from the group consisting of protoplasts from a second species of Poxphyra or protoplasts from an algal species other than Porphyra;
    isolating selected fusion products produced in said fusion step;
    culturing said selected fusion products to produce multicellular material; and
    determining the manner in which said multicellular material represents a new or modified strain of Poxphyra.

2. The method of claim 1 wherein said second protoplasts are from a second species of Porphyra.

3. The method of claim 2 wherein said second protoplasts are from conchocelis.

4. The method of claim 2 wherein said second protoplasts are from conchospores.

5. The method of claim 2 wherein said second protoplasts are from blade.

6. The method of claim 1 wherein said preparing step includes the steps of:
    providing conchocelis stocks from free-living cultures;
    manually separating conchosporangial branch conchocelis from the conchocelis stocks;
    subcloning said conchosporangial branch conchocelis until pure cultures are developed;
    maintaining said pure cultures within a temperature range of from 20–24° C. and a long day photoperiod of 14–16 hrs light at a light level of 8–20 $\mu$Einsteins;
    fragmenting conchosporangial filaments from said pure cultures; and
    enzymatically releasing protoplasts from said fragmented filaments.

7. The method of claim 1 wherein said fusion step includes the steps of:
    combining said first and second protoplasts under low light conditions;
    treating said combined first and second protoplasts with a solution of a chemical fusogen effective to cause their agglutination;
    treating the agglutinated first and second protoplasts with an hypotonic fusion solution to cause said protoplasts to fuse;
    after fusion is observed, replacing said hypotonic fusion solution with a hypertonic washing solution to provide a hypertonic environment; and
    replacing said hypertonic washing solution with culture medium effective to stimulate cell wall formation and cell division.

8. The method of claim 7 wherein said chemical fusogen is selected from the group consisting of polyethylene glycol, sodium nitrate, dextran, high pH-high calcium containing solutions and combinations thereof.

9. The method of claim 1 wherein said fusing step comprises electrofusion.

10. The method of claim 1 wherein said multicellular material is an undifferentiated cell mass.

11. The method of claim 1 wherein said multicellular material is a whole plant.

* * * * *

UNITED STATES PATENT AND TRADEMARK OFFICE
CERTIFICATE OF CORRECTION

PATENT NO.    : 6,531,646 B1                                          Page 1 of 1
DATED         : March 11, 2003
INVENTOR(S)   : Donald P. Cheney et al.

It is certified that error appears in the above-identified patent and that said Letters Patent is hereby corrected as shown below:

<u>Column 4,</u>
Lines 28 and 30, "18srDNA" should read -- 18s rDNA --;

<u>Column 15,</u>
Line 7, "18srDNA" should read -- 18s rDNA --;
Line 13, "P. yezoensis" should read -- *P. yezoensis* --;
Line 37, "#19-6" should read -- #15-6 --;
Line 59, "#24.1" should read -- #24-1 --;

<u>Column 17,</u>
Lines 35 and 43, "Poxphyra" should read -- Porphyra --;

Signed and Sealed this

Twentieth Day of April, 2004

JON W. DUDAS
*Acting Director of the United States Patent and Trademark Office*